US 8,377,655 B2
Feb. 19, 2013

United States Patent
Wood et al.

(54) ASSAY FOR THE MEASUREMENT OF IGF TYPE 1 RECEPTOR AND INSULIN RECEPTOR EXPRESSION

(75) Inventors: Teresa L. Wood, Cedar Grove, NJ (US); Anne M. Rowzee, Rockville, MD (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 12/721,327

(22) Filed: Mar. 10, 2010

(65) Prior Publication Data

US 2011/0223604 A1 Sep. 15, 2011

Related U.S. Application Data

(60) Provisional application No. 61/209,807, filed on Mar. 10, 2009.

(51) Int. Cl.
*C12P 19/34* (2006.01)
(52) U.S. Cl. ........................................... 435/91.2
(58) Field of Classification Search .................. 435/91.2
See application file for complete search history.

(56) References Cited

PUBLICATIONS

Neuvians et al., Neoplasia, vol. 7, pp. 446-456, May 2006.*
Neuvians et al., Endocrine, vol. 22, pp. 93-99, Nov. 2003.*
Wiersma et al., The American Physiological Society, vol. 272, (Endocrinol. Metab. 35): pp. E607-E615, 1997.*
Bailyes et al. "Insulin Receptor/IGF-I Receptor Hybrids are Widely Distributed in Mammalian Tissues: Quantification of Individual Receptor Species by Selective Immunoprecipitation and Immunoblotting" Biochemistry Journal 1997 vol. 327:209-215.
Benyoucef et al. "Characterization of Insulin/IGF Hybrid Receptors: Contributions of the Insulin Receptor L2 and Fn1 Domains and the Alternatively Spliced Exon 11 Sequence to Ligand Binding and Receptor Activation" Biochemistry Journal 2007 vol. 403:603-613.
Frasca et al. "Insulin Receptor Isoform A, a Newly Recognized, High-Affinity Insulin-Like Growth Factor II Receptor in Fetal and Cancer Cells" Molecular and Cellular Biology 1999 vol. 19(5):3278-3288.
Pandini et al. "Insulin/Insulin-like Growth Factor I Hybrid Receptors Have Different Biological Characteristics Depending on the Insulin Receptor Isoform Involved" The Journal of Biological Chemistry 2002 vol. 277(42):39684-39695.
Soos et al. "Purified Hybrid Insulin/Insulin-like Growth Factor-I Receptors Bind Insulin-like Growth Factor-I, But Not Insulin, With High Affinity" Biochemistry Journal 1993 vol. 290:419-426.
Vandenbroucke et al. "Quantification of Splice Variants Using Real-Time PCR" Nucleic Acids Research 2001 vol. 29(13):e68.

* cited by examiner

*Primary Examiner* — Gary Benzion
*Assistant Examiner* — Cynthia Wilder
(74) *Attorney, Agent, or Firm* — Licata & Tyrrell P.C.

(57) ABSTRACT

This invention relates to a quantitative PCR assay that differentiates between IR-A, IR-B and IGF-IR mRNAs and compares expression of the three receptors on the same scale.

2 Claims, 6 Drawing Sheets

$Y = -6.954 - 0.013 * X; R^2 = 1.874E-4$

SEQUENCE LISTING

```
<160> NUMBER OF SEQ ID NOS: 14

<210> SEQ ID NO 1
<211> LENGTH: 29
<212> TYPE: DNA
<213> ORGANISM: Mouse

<400> SEQUENCE: 1
aggtccaacg accccaagtc tcagacccc                                      29

<210> SEQ ID NO 2
<211> LENGTH: 35
<212> TYPE: DNA
<213> ORGANISM: Mouse

<400> SEQUENCE: 2
aatggtagag gagacgttgg ggaaatctgg aagtg                               35

<210> SEQ ID NO 3
<211> LENGTH: 31
<212> TYPE: DNA
<213> ORGANISM: Mouse

<400> SEQUENCE: 3
ccctcaccat ggtggaaaac gaccatatcc g                                   31

<210> SEQ ID NO 4
<211> LENGTH: 35
<212> TYPE: DNA
<213> ORGANISM: Mouse

<400> SEQUENCE: 4
tgtgatattg taggtgtcag ctaccgtggt gttcc                               35

<210> SEQ ID NO 5
<211> LENGTH: 21
<212> TYPE: DNA
<213> ORGANISM: Mouse

<400> SEQUENCE: 5
tcctgaagga gctggaggag t                                              21

<210> SEQ ID NO 6
<211> LENGTH: 17
<212> TYPE: DNA
<213> ORGANISM: Mouse
```

```
<400> SEQUENCE: 6
ctttcgggat ggcctgg                                              17

<210> SEQ ID NO 7
<211> LENGTH: 19
<212> TYPE: DNA
<213> ORGANISM: Mouse

<400> SEQUENCE: 7
ttcgggatgg cctactgtc                                            19

<210> SEQ ID NO 8
<211> LENGTH: 23
<212> TYPE: DNA
<213> ORGANISM: Mouse

<400> SEQUENCE: 8
ggcacaacta ctgctccaaa gac                                       23

<210> SEQ ID NO 9
<211> LENGTH: 24
<212> TYPE: DNA
<213> ORGANISM: Mouse

<400> SEQUENCE: 9
ctttatcacc accacacact tctg                                      24

<210> SEQ ID NO 10
<211> LENGTH: 20
<212> TYPE: DNA
<213> ORGANISM: Mouse

<400> SEQUENCE: 10
gtcacattcc caacatcgcc                                           20

<210> SEQ ID NO 11
<211> LENGTH: 19
<212> TYPE: DNA
<213> ORGANISM: Mouse

<400> SEQUENCE: 11
ttttcgtccc caggccatc                                            19

<210> SEQ ID NO 12
<211> LENGTH: 21
<212> TYPE: DNA
<213> ORGANISM: Mouse

<400> SEQUENCE: 12
ccccagaaaa acctcttcag g                                         21

<210> SEQ ID NO 13
<211> LENGTH: 23
<212> TYPE: DNA
<213> ORGANISM: Mouse

<400> SEQUENCE: 13
ggcacaatta ctgctccaaa gac                                       23

<210> SEQ ID NO 14
<211> LENGTH: 19
<212> TYPE: DNA
<213> ORGANISM: Mouse
```

| -continued | |
|---|---|
| <400> SEQUENCE: 14 | |
| caaggccctt tctcccaac | 19 |

ASSAY FOR THE MEASUREMENT OF IGF TYPE 1 RECEPTOR AND INSULIN RECEPTOR EXPRESSION

CROSS-REFERENCE TO RELATED APPLICATION

Figure 1:
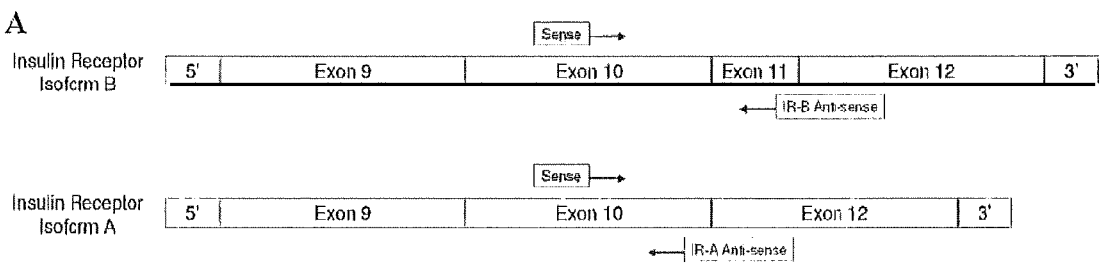
Figure 1:
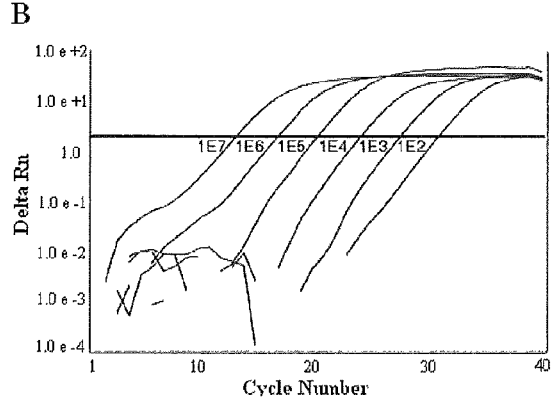
Figure 1:
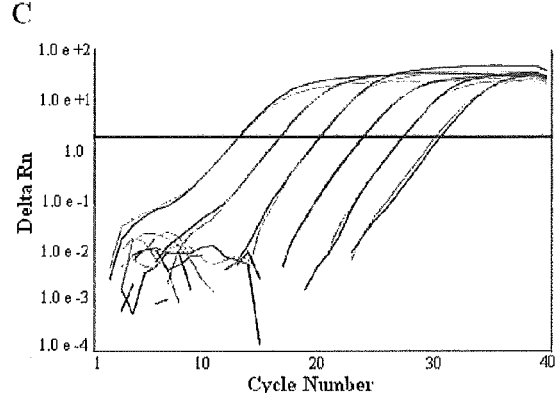
Figure 1:
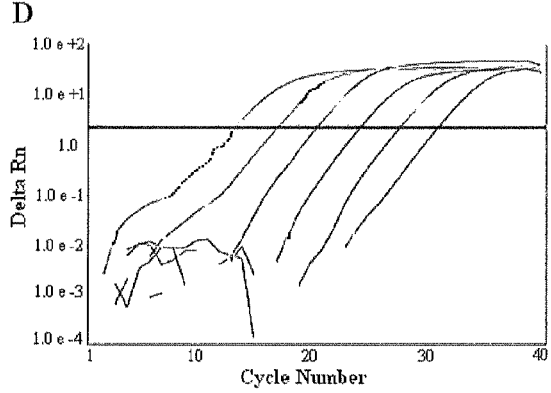
Figure 1:
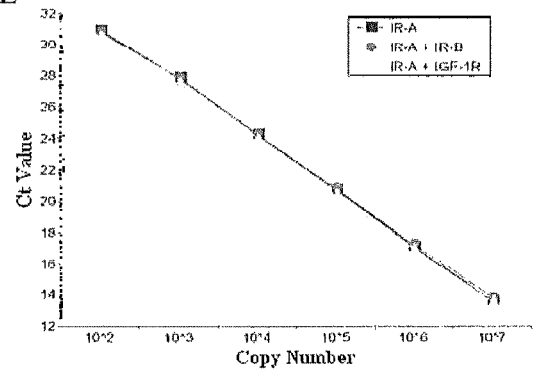

The instant application claims 35 U.S.C. §119(e) priority to U.S. Provisional Patent Application Ser. No. 61/209,807 filed Mar. 10, 2009, the disclosure of which is incorporated herein by reference.

STATEMENT REGARDING FEDERALLY SPONSORED RESEARCH OR DEVELOPMENT

This invention was produced in part using funds obtained through grant DK060612 from the National Institutes of Health. The federal government may have certain rights in this invention.

This invention relates to a quantitative PCR assay that differentiates between IR-A, IR-B and IGF-IR mRNAs and compares expression of the three receptors on the same scale.

Early studies have supported the long-held view that, at physiologically relevant levels, insulin signaled through the insulin receptor (IR) while the two IGF ligands, IGF-I and IGF-II, exerted biological actions through the type I insulin-like growth factor receptor (IGF-IR). An emerging problem in the field of insulin and IGF signaling is the existence of multiple forms of signaling receptors through which these molecules exert biological actions. Moreover, ligand "cross-talk" to the alternate receptor (insulin to the IGF-IR and IGFs to the IR) was thought to occur only at superphysiological ligand concentrations. Thus, this was a consideration only for specific conditions in vivo such as diabetes and for in vitro studies where micromolar levels of insulin are commonly used.

A number of recent studies have led to a revision of this model for insulin and IGF signaling. These new data provide evidence for: 1) the existence of Hybrid-Rs (IGF-IR/IR) in most tissues [1, 2], 2) preferential affinity of IGF-I and IGF-II versus insulin to the Hybrid-Rs [1, 3], 3) an alternate splice form of the IR (IR-A isoform) lacking exon 11 (12 amino acids), which binds IGF-II as well as insulin at physiological concentrations [4, 5], and 4) proportionately higher levels of the IR-A isoform in developing tissues, in certain cancers, including breast cancers [4], and in insulin or IGF-sensitive tissues in diabetic animals (unpublished data). These data have dramatically shifted current thinking about insulin and IGF actions and have led to the important question of how activation of these various receptors differ in their downstream signaling pathways and biological actions in target tissues in both normal and disease states.

Due to the high degree of sequence and structural homology between the IR and IGF-IR, hybrid receptors form as mentioned. Hybrid receptors consist of equal parts IR and IGF-IR and have high affinity for IGF ligands. The prevailing model for formation of hybrid receptors is based on a stochastic model of heterotetramer formation. This model predicts hybrid receptor formation based on the relative expression of the IR and the IGF-IR and requires knowledge of IGF-IR and IR expression on the same scale. In all previous studies, IR isoform (A and B) and IGF-IR expression have been measured separately, and currently no assay exists to quantify levels of expression of all three receptor forms on the same scale. Such an assay would predict specific ligand actions, receptor signaling activation as well as the existence of hybrid receptors. To date, there has been no assay to determine either relative or absolute expression levels of all three receptors, exon 11$^-$ IR isoform-A (IR-A), exon 11$^+$ IR isoform-B (IR-B) and IGF-IR, within a particular tissue or cell type.

Thus, there is considerable interest in defining the expression levels of IGF1R and IR isoforms in rodent as well as human tissues and tumors. However, the relative quantity of the receptors has never before been measured together on the same scale in either rodent or human cell lines or specimens. The ability to do so would allow for associating different tissues, cell types or cancers with specific "molecular signatures" of IGF/insulin signaling receptors.

Thus it is an object of the instant invention to provide for an assay to determine relative expression levels of the three rodent receptors, exon 11$^-$ IR isoform-A (IR-A), exon 11$^+$ IR isoform-B (IR-B) and IGF-IR, within a particular tissue or cell type.

It is an additional object of the instant invention to provide for an assay to determine relative expression levels of the three human receptors, exon 11$^-$ IR isoform-A (IR-A), exon 11$^+$ IR isoform-B (IR-B) and IGF-IR, within a particular tissue or cell type.

There now has been developed a highly specific quantitative PCR assay that differentiates between rodent IR-A, IR-B and IGF-IR mRNAs and compares expression of all three receptors on the same scale.

In an additional embodiment of the invention a highly specific RT-PCR assay to quantify human IR-A, IR-B and IGF-1R on the same scale using specially designed primers has been developed.

The availability of such a highly specific quantitative PCR assay i.e. reagents to quantify levels of the IR isoforms and IGF-IR on the same scale can provide a critical diagnostic and predictive tool for a variety of clinically relevant questions. These reagents can be used: 1) to predict insulin and IGF sensitivity of cells or tissues, 2) to predict the existence and levels of hybrid receptors, 3) to guide treatment strategies and predict potential treatment success for cancer, diabetes and metabolic diseases, 4) in analysis of animal models of relevant diseases, 5) in high through-put screening of new compounds and development of new specific drugs for treatment of diabetes and cancer.

Figure 2:
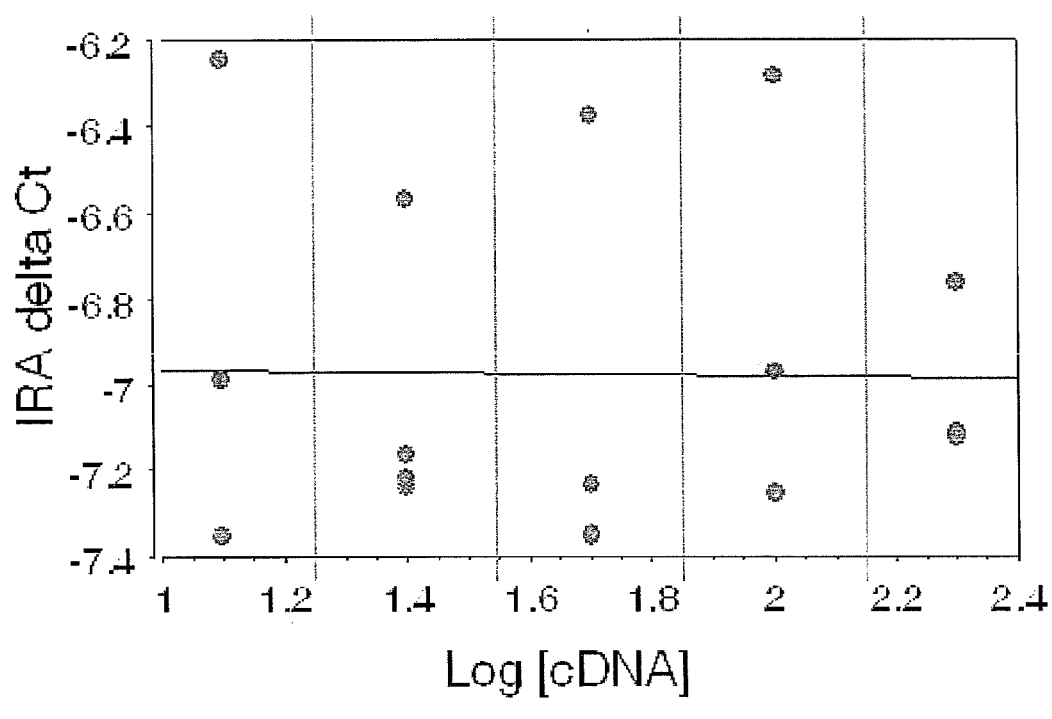
Figure 3:
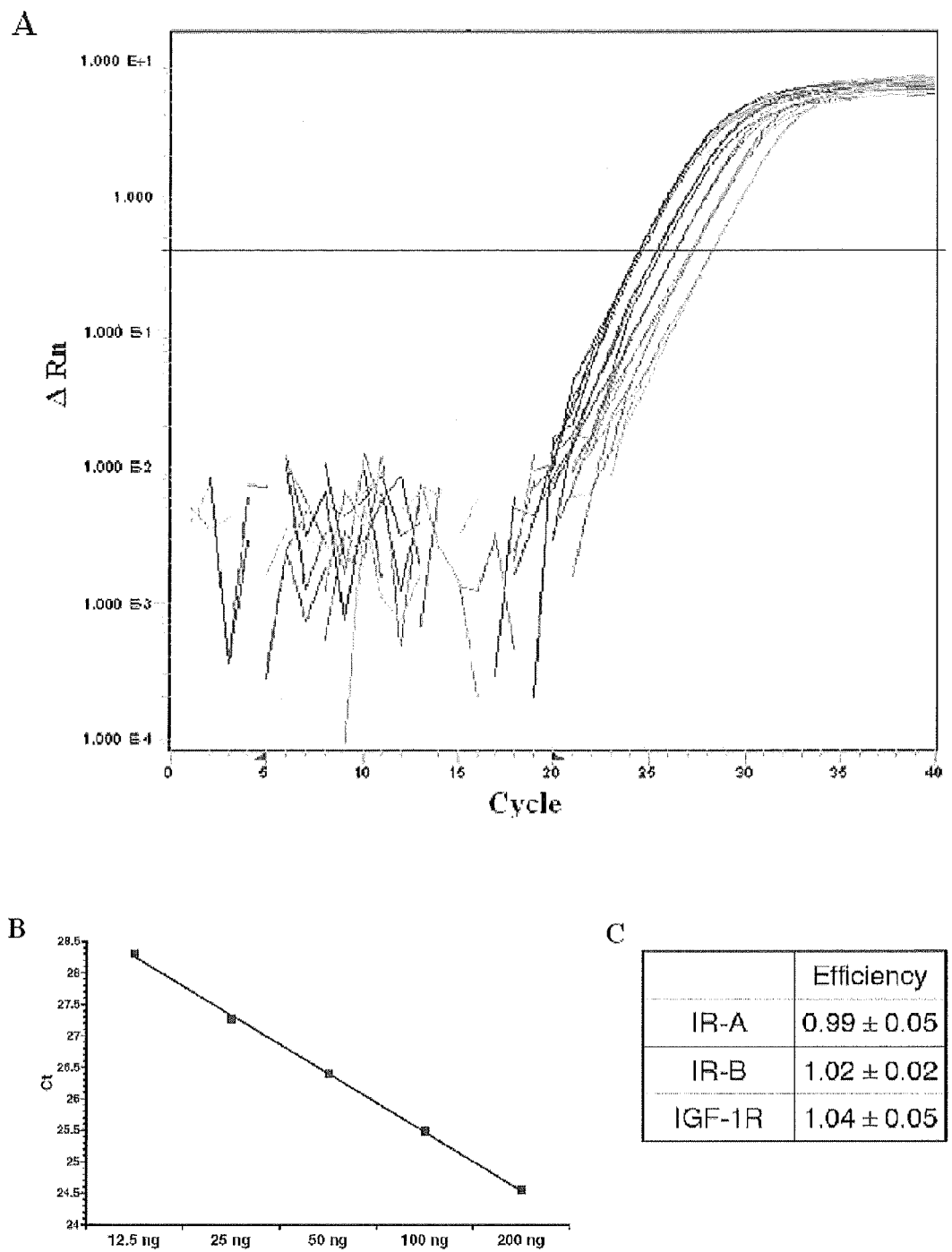

Specifically, this assay will allow determination of IGF-IR, IR-A and IR-B mRNA expression in:

1) cells or tissues of the mouse including wild-type mice of any strain and transgenic or knock-out mouse models 2) cells or tissues of mouse or rat models of obesity, diabetes, cancer or other diseases where metabolic alterations might have a role 3) tumor cells, normal cells or tissues of mouse 4) tumor cells, normal cells or tissues of rats 5) human or primate cells and tissues 6) human or primate tumors 7) tumors for profiling and to predict therapy response or efficacy 8) insulin target and non-target tissues to predict insulin sensitivity 9) IGF-sensitive tissues to predict sensitivity to IGF-I or IGF-II 10) developing tissues or fetal tissue to predict developmental or growth abnormalities The invention is defined more fully below in conjunction with the Figures wherein:

FIG. 1 shows rodent insulin receptor isoform-specific Q-PCR assays wherein (A) Schematic representation of IR-B (exon 11$^+$) and IR-A (exon 11$^-$) primer design strategy. Both assays use a common sense primer that anneals within exon 10 and isoform-specific anti-sense primers that anneal across exon-exon junctions unique to each isoform. (B) Sample amplification plot for IRA assay using ten-fold serial dilution of IR-A standard as template. Horizontal line indicates threshold determined by Applied Biosystems Sequence Detection Systems Software. Numbers to the left of each amplification curve indicate amount of standard used as template in each reaction. (C, D) Competition assays. Amplification plot shown in (B, blue) overlaid with amplification plot using IR-A standards plus $10^7$ copies of IR-B (C, green) or of IGF-1R (D, yellow) standard at each data point. Graphs in (B-D) were generated using Applied Biosystems Sequence Detection Systems Software. (E) IR-A standard curves from data generated in (B-D). Plots demonstrate Ct value v. IR-A copy number. ■,: data generated in (B); ●,: data generated in (C); ▲,: data generated in (D);

FIG. 2 shows rodent IR-A primers are suitable for the comparative Ct method of quantitation wherein two-fold serial dilutions of Calibrator cDNA (200 ng-12.5 ng) were analyzed by Q-PCR for IR-A and β-actin amplification. For each blue data point, the log [cDNA dilution] was plotted against the ΔCt value (average Ct β-actin–average Ct IR-A, from three replicates). Data at each cDNA concentration are from four independent serial dilutions of cDNA. Vertical lines have been added to separate data at each concentration. A linear regression (horizontal line, equation below graph) was fit to data. The absolute value of the slope of the regression must be <0.1 for the comparative Ct method to be valid. As shown, this value for IR-A is 0.013; and FIG. 3 shows Q-PCR assay efficiency in total RNA samples pooled from murine cell lines wherein A. Log ΔRn v. cycle amplification plot for IR-A Q-PCR assay using two-fold serial dilution of Calibrator cDNA as template. Horizontal line indicates threshold setting. B. Standard curve from data generated in (A), plot demonstrates Ct value v. ng of Calibrator cDNA. C. Efficiency of primer pairs using mixed pool of cDNA as template. Values are mean±S.E. from five independent reactions.

Figure 4:
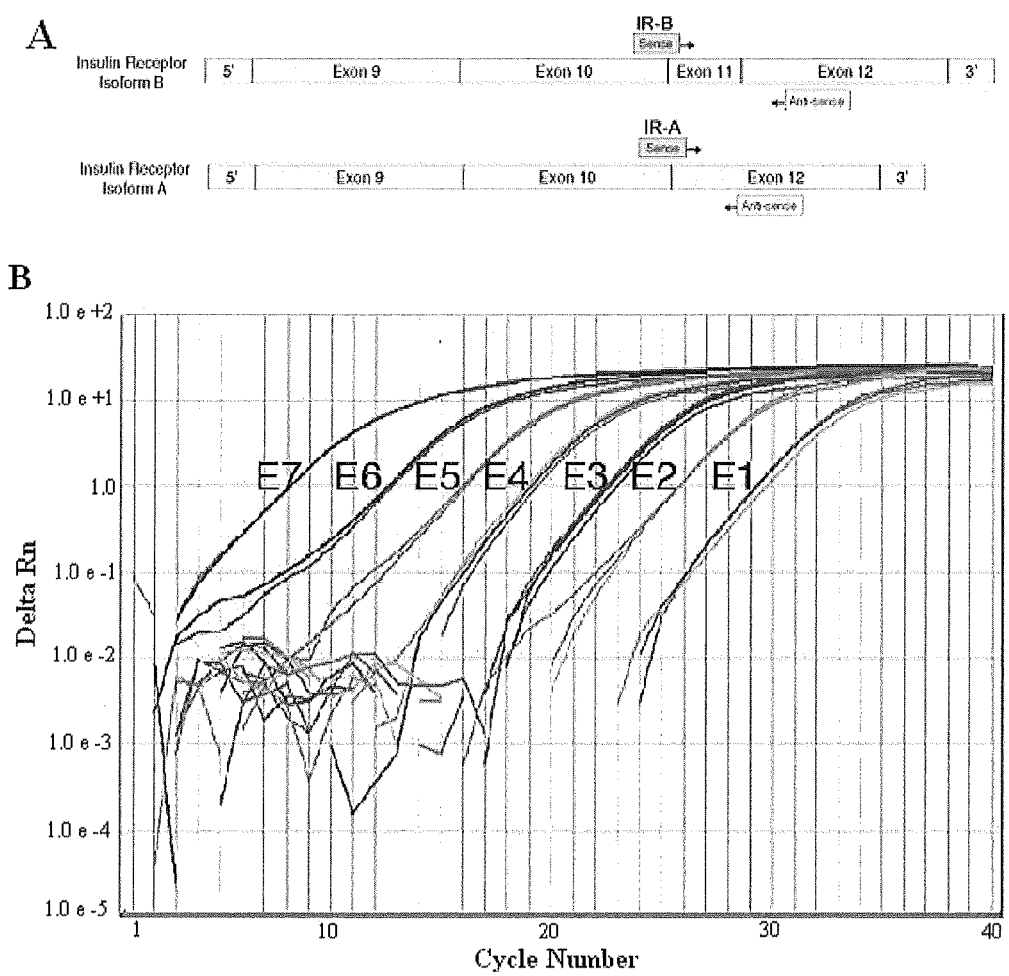
Figure 4:
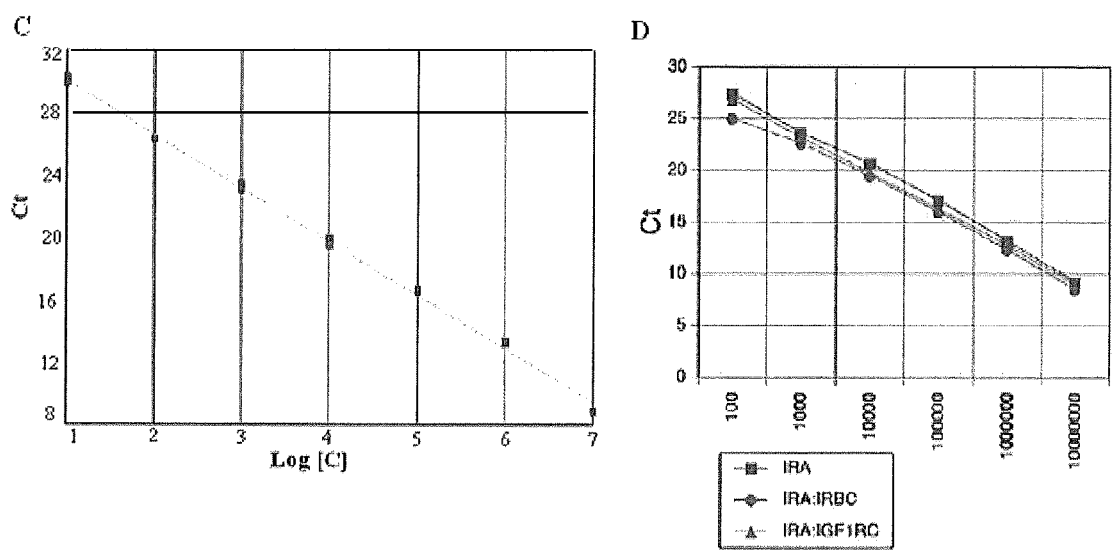

FIG. 4 shows human insulin receptor isoform-specific Q-PCR assays wherein (A) Schematic representation of IR-B (exon 11$^+$) and IR-A (exon 11$^-$) primer design strategy. Both assays use a common antisense primer that anneals within exon 12 and isoform-specific sense primers that anneal across exon-exon junctions unique to each isoform. (B) Sample amplification plot for IR-A assay using ten-fold serial dilution of IR-A standard as template. Horizontal line indicates threshold determined by Applied Biosystems Sequence Detection Systems Software. Numbers to the left of each amplification curve indicate amount of standard used as template in each reaction. (C) A standard curve generated from the amplification plot of Ct vs. log concentration of the plasmid standards for IR-A. (D) Competition assays. Amplification plot for IR-A (blue) overlaid with amplification plot using IR-A standards plus $10^7$ copies of IR-B (red) or of IGF-1R (green) standard at each data point.

Figure 5:
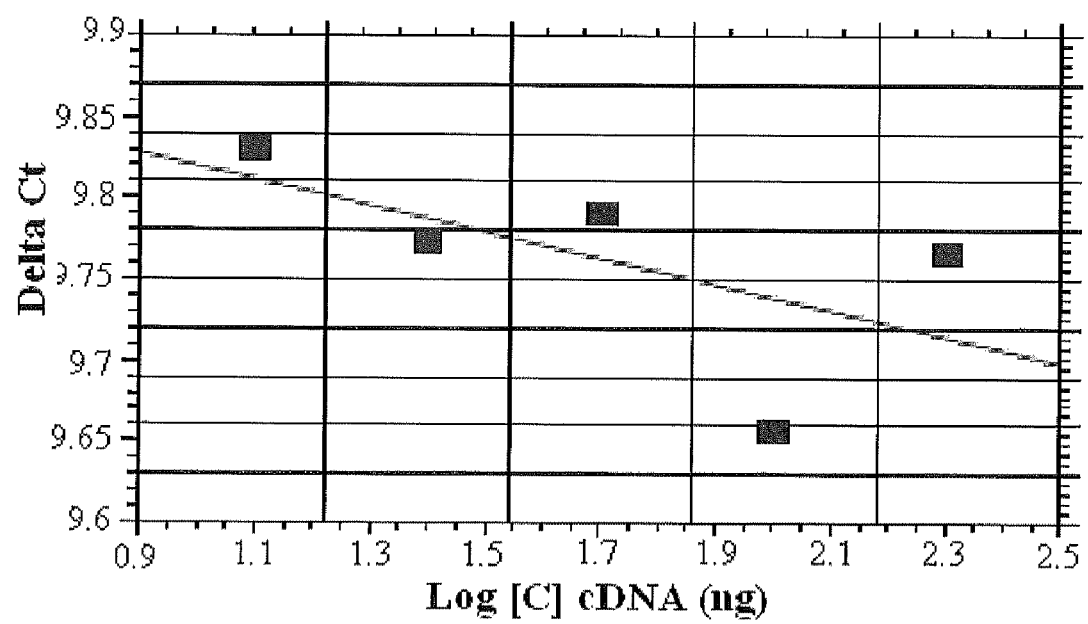

FIG. 5 shows the efficiency plot of human IGF1R and β-Actin, plotting Delta Ct vs. log concentration ng cDNA. The slope of the regression line is −0.0808.

Rodent Insulin Receptor Isoform and IGF-1R
Q-PCR Assay Development and Optimization Due to the small sequence difference between IR-A and IR-B and the high degree of sequence homology between the IGF-IR and IR mRNAs, primer design was critical to developing a Q-PCR assay to detect all three receptors. For the IR isoform-specific assays, a common sense primer was designed that anneals within exon 10 to reduce inter-assay variability and to obtain similar PCR kinetics. Vandenbroucke and colleagues [6] determined the most accurate method was to use a primer that spans the exon junction specific to each isoform, particularly if the isoforms differ greatly in abundance. We adopted this strategy for the IR isoform-specific assays and designed a common sense primer that anneals within exon 10 to reduce inter-assay variability and obtain similar PCR kinetics. Specific anti-sense primers were designed against exon/exon junctions unique to each isoform (FIG. 1A) and IGF-1R primers were targeted to a region of low IR homology.

Assay Specificity

Each primer pair was validated based on specificity, sensitivity and efficiency. Assay specificity was determined by dissociation curves, electrophoresis, and sequencing of Q-PCR products. Dissociation curves from assays performed on the same Q-PCR plate were overlaid to illustrate that each assay gave a single sharp peak indicating a single PCR product per reaction. (FIGS. 2A, B) Products from the IR-A assay gave a dissociation curve with a melting temperature ($T_m$) distinct from IR-B (FIG. 2A). IGF-IR and IR-B reaction products also had distinct $T_m$s (FIG. 2B). If any of the primer pairs cross-reacted with a non-specific target or with contaminating genomic DNA, the individual dissociation curves would have consisted of more than one peak each with a different $T_m$ or a plateau indicating many reaction products with varying melting temperatures. An overlay of dissociation curves from all three assays exhibited a sharp IGF-IR peak located between the IR-A and IR-B peaks, as expected from their predicted product size.

To confirm primer specificity, Q-PCR products were taken directly from a post-amplification assay plate and analyzed by gel electrophoresis (FIG. 2C). As expected from dissociation curve analysis, a single band of appropriate size was present for each assay. Q-PCR reaction products for IR-A, IR-B, IGF-IR and β-actin were cloned and sequenced. Sequences were confirmed and plasmid clones were used for tests of sensitivity and efficiency.

Assay Sensitivity and Reaction Efficiency

Confirmed plasmids were linearized and 10-fold serial dilutions were used as standards in primer sensitivity tests. Q-PCR amplification plots of IR-A standards demonstrate this assay is accurate over six orders of magnitude down to $10^2$ copies (FIG. 1B). IR-B and IGF-IR assays were also both accurate over six orders of magnitude down to $10^2$ copies and resulted in similar standard curves. Lower copy numbers were difficult to precisely seed onto reaction plates and therefore did not give reliable replicate amplification curves. However, the $R^2$ values for IR-A, IR-B and IGF-IR standard curves were between 0.95 and 0.99. This high linearity indicates that small amounts of receptor RNA targets could still be reliably amplified from within a larger pool of mixed template.

The slope of the standard curve was used to determine reaction efficiency using the following equation: $E=[10^{-(1/slope)}]-1$, where $E=1.0$ when slope$=-3.33$ indicating 100% reaction efficiency. It is critical for Absolute Quantification (A.Q.) Q-PCR assays and for the Standard Curve Method of Relative Quantification that efficiency of all primer pairs be equivalent to allow accurate comparison between expression levels of each gene target. Although the use the $\Delta\Delta C_t$ method of relative quantification was chosen for the analyses due to the use of commercially available primers to test primary mammary epithelial cells (MEC) sample purity, it was also very important that reaction efficiency be similar for all receptor and endogenous control primer pairs. The efficiency IGF-IR primers is 0.965±0.054. β-actin was chosen as the endogenous control gene for the relative quantification (R.Q.) studies; the efficiency of the β-actin reaction was 0.98 using plasmid standards as template. All primers had statistically similar efficiency when using standards containing exact targets as template, indicating that these primer pairs are suitable for use in A.Q. and both methods of R.Q.

Competition assays were used to test the capability of our primers to specifically amplify their target in the presence of excess non-specific, homologous target, as may be the case when analyzing total RNA from a biological sample. Serial dilution of standards was repeated in a fixed excess of $10^7$ copies of competitor plasmid and standard curves were generated (1, 2). The standard curve from IR-A amplification plots (FIG. 1B) is shown in FIG. 1E (■). Amplification plots were generated from serial dilution of IR-A standards in a fixed concentration of IR-B plasmid competitor (FIG. 1C) or IGF-1R plasmid competitor (FIG. 1D). There was no significant change in IR-A amplification curves with addition of either competitor. Thus, there was no change in the IR-A standard curve (FIG. 1E, compare ■ with ● or ▲) resulting from this data indicating specific amplification of IR-A product. Similarly, the efficiency of IR-B and IGF-1R assays was not significantly changed in the presence of competition. These data demonstrate that the primers designed here are sensitive and precise to detect 100 copies of their target in the presence or absence of $10^5$ excess copies of highly homologous targets.

It is critical that efficiency of all primer pairs be approximately equivalent to allow accurate comparison of gene expression using the ΔΔCt method of relative quantification (Applied Biosystems User Bulletin 2 P/N 4303859), therefore each primer pair designed for these studies was validated based on efficiency as well as sensitivity, and specificity. Primer efficiency is determined by the following equation: $E=[10^{-(1/slope)}]-1$; where slope is the slope of the standard curve when Ct value is plotted versus known amount of template, and E=1.0 when slope is approximately −3.33 (i.e. 100% reaction efficiency). The efficiency of β-actin primers using cDNA as template is 9713, and the efficiencies of IR-A, IR-B and IGF-1R primers are 99±3, 102±2 and 104±5, respectively (FIG. 3). An additional test to determine if the efficiencies of the endogenous control primers and IR isoform and IGF-1R primers are suitably equivalent for the ΔΔCt method of relative quantification is to plot the log cDNA dilution versus the ΔCt value (Ct of target ΔCt of endogenous control) and fit the data with a linear regression curve (Sample graph, FIG. 2). According to Livak and Schmittgen [7], if the absolute value of the slope of the linear regression is close to zero, then the reaction efficiencies of the target and endogenous control genes are similar and the ΔΔCt method of calculation can be applied. We have performed this analysis at least three times for each receptor primer pair using two-fold serial dilution of 200 ng–12.5 ng cDNA and the absolute values of the slope of the linear regression lines are 0.013 (FIG. 2), 0.03 and 0.039, for IR-A, IR-B and IGF-1R respectively. These values are well below the value of 0.1 recommended in Applied Biosystems User Bulletin 2, indicating that the primers designed here for quantification of IR isoform and IGF-1R mRNA are suitable for use in the ΔΔCt method of R.Q.

Materials and Methods
Q-PCR Assay Primers

IR-A and IGF-IR mRNA sequences used for primer design are located on the National Center for Biotechnology Information (NCBI) website, accession numbers NM_010568 and NM_01053, respectively. There is no full-length mouse IR (IR-B) transcript published at NCBI, therefore we aligned the human IR-B transcript (accession number NM_000208) with the mouse IR-A sequence to identify the exon 10/exon 12 junction by a 36 by mismatch in the alignment. We then inserted the mouse exon-11 sequence (accession number L42997) within this junction to create a full-length mouse IR-B sequence. Translation of the mouse IR-B mRNA sequence along the first open reading frame produces an amino acid sequence with 94% homology to the human IR-B protein sequence and with the predicted 12-residue mismatch when aligned with the mouse IR-A protein sequence.

IR-A, IR-B and IGF-IR Q-PCR primers were designed using Primer Premier v.5 Software (Premier Biosoft International, Palo Alto, Calif.) with attention to standard criteria for Q-PCR primer design as outlined in the QuantiTect SYBR Green PCR handbook (Qiagen, Valencia, Calif.). For IR-A and IR-B, a common sense primer that anneals within exon 10 was used with isoform-specific anti-sense primers. To detect IR-A, we designed an anti-sense primer to anneal across the exon 10/12 junction. For detection of IR-B, we targeted the exon 11/12 junction since the 3' end of this anti-sense primer anneals within exon 11, the exon absent in TR-A. To design TGF-TR primers, mouse IR-B and IGF-IR mRNA sequences (NCBI ID# NM_010568+L42997 and NM_01053, respectively) were aligned to target a region of low homology to prevent cross-reactivity of IGF-IR primers with either IR isoform. All primers designed for these analyses either span exon/exon junctions or anneal to two different exons to prevent interference from contaminating genomic DNA. Primers were purchased from Integrated DNA Technologies, Inc. (Coralville, Iowa) and re-suspended in Tris-EDTA to a concentration of 100 μM.

Quantitative PCR

Unless otherwise noted all reactions were performed on the Applied Biosystems 7900HT Fast Real-time PCR system using associated Sequence Detection Systems Software Version 2.2.2 (SDS2.2.2, Foster City, Calif.). The thermal profile for all reactions was as follows: 50° C. for 2 minutes, 95° C. for 10 minutes, 40 cycles of 95° C. for 15 seconds and 58° C. (annealing temperature) for 1 minute.

To obtain a dissociation curve, a temperature ramp (95° C. for 15 seconds, 60° C. for 15 seconds, ramp to 95° C.) with continuous fluorescence detection was added to the thermal profile following amplification cycles. At the start of the temperature ramp, reaction products were double stranded and fluorescence was high due to bound SYBR green. As reaction products melted, SYBR green was released with a subsequent rapid decrease in fluorescence. The first derivative of fluorescence versus time was plotted to give curves with a peak at the $T_m$ of the reaction products.

Unless otherwise indicated, IR-A, IR-B, IGF-IR, and β-actin reactions contained final concentrations of the following: 1× QuantiTect SYBR Green PCR Master Mix (Qiagen, Valencia, Calif.), 0.25 μM each sense and anti-sense primers, and 50 ng cDNA. Q-PCR reactions performed to generate standard curves (to test for sensitivity and efficiency) were run either on the Applied Biosystems 7900HT Fast Real-time PCR system or on the Applied Biosystems 7300 Real-time PCR system using associated Sequence Detection Systems Software version 1.2.3 and included a dissociation stage using the absolute quantification assay.

Q-PCR reactions performed to quantify target gene expression were analyzed using the SDS 2.2.2 relative quantification (ΔΔCt) assay. Data from individual ΔΔCt assays were combined into an SDS relative quantification (ΔΔCt) study to determine the expression level of each target mRNA in all primary MEC samples. The analysis settings were as follows: automatic threshold and baseline determined by SDS 2.2.2 software, calibrator sample is "Calibrator" cDNA (detailed description in Results section), β-actin is endogenous control, and RQ Min/Max confidence set to 95%. All absolute quantification and ΔΔCt assays were carried out at least twice and each sample was run in quadruplicate.

Primer Validation

Optimal primer concentrations were determined using serial dilution of each primer in the presence of a fixed concentration of its partner, from three independent absolute quantification assays (data not shown). For all receptor and β-actin primers, 0.25 µM sense and anti-sense primers gave specific amplification at or near the same cycle threshold of all other primer pairs. Samples for agarose gel electrophoresis were removed directly from a post-amplification Q-PCR plate, mixed with loading dye and run on a 2% agarose gel with ethidium bromide at 100V for 1.5 hours. Images were obtained using a UVP EpiChemi Darkroom system and associated UltraQuant Molecular Imaging and Analysis Software (Upland, Calif.).

Q-PCR standards for sensitivity and efficiency analysis were generated from post-amplification Q-PCR samples. IR-A, IR-B, IGF-IR and β-actin Q-PCR products were removed from the Q-PCR plate and purified using the MinElute PCR Purification Kit, microcentrifuge protocol (Qiagen, Valencia, Calif.). Four microliters of purified products were cloned into the pCR2.1-TOPO vector (Invitrogen, Carlsbad, Calif.) and 2 µl of the subsequent plasmid was used to chemically transform One Shot TOP10 competent cells (Invitrogen, Carlsbad, Calif.). Transformed cells were spread on 50 µg/ml ampicillin LB plates and incubated overnight at 37° C. Ten positive colonies from each transformation were used to seed 3 ml LB+50 µg/ml kanamycin cultures. Cultures were grown overnight at 37° C. with shaking at 225 rpm. Plasmid DNA was isolated from 6 cultures per transformation using QIAprep Spin Miniprep Kit, microcentrifuge protocol (Qiagen, Valencia, Calif.). Plasmid DNA was digested with BamHI and XhoI restriction enzymes (Promega, Madison, Wis.) at 37° C. for 1 hour and then analyzed on a 1% agarose gel run at 100V for 1.25 hours to verify the presence of an insert. One insert-containing clone from each transformation was sequenced for verification using the M13 Reverse primer. Plasmid DNA was linearized using the XhoI restriction enzyme (Promega, Madison, Wis.) and analyzed on 1% agarose gel as above. Linearized DNA was purified using the MinElute Reaction Cleanup Kit, microcentrifuge protocol (Qiagen, Valencia, Calif.) and quantified by spectrophotometry. Copy number was calculated using the following formula, (DNA concentration (g/µl)/[plasmid length (bp)*660])*$6.022 \times 10^{23}$=molecules/µl.

Linear plasmid DNA was diluted to $10^7$ molecules/µl and subsequent 10-fold serial dilutions were used as standards to test the detection limit and efficiency of each primer pair. Standards were used as template in SDS2.2.2 absolute quantification assays with reaction conditions as described above including a dissociation stage. The threshold cycle (Ct) value from amplification curves at each data point was plotted versus Log copy number of plasmid template to generate a standard curve and calculate reaction efficiency. Efficiency was also evaluated for each primer pair using two-fold dilutions of 200 ng Calibrator cDNA as template.

To test IR isoform-specific primer sensitivity, $10^7$ copies of the non-specific plasmid DNA target was mixed with each standard and used as template in SDS2.2.2 absolute quantification assays. $10^7$ copies of IR-B plasmid DNA was mixed with each of the IR-A standards and used in the IR-A Q-PCR assay. To test IR-B primer sensitivity, $10^7$ copies of IR-A plasmid DNA was mixed with the IR-B standards and used in the IR-B Q-PCR assay. Standard curves as described above.

Development of Q-PCR Standards

The following primers to the region encompassing the 3' end of exon eight to the 5' end of exon 11 (exon 12 in IR-B) of the IR and IGF-1R were used to synthesize plasmid standards for Q-PCR:

```
IR standard sense
                                    (SEQ ID NO. 1)
5'AGGTCCAACGACCCCAAGTCTCAGACCCC3'
and antisense
                                    (SEQ ID NO. 2)
5'AATGGTAGAGGAGACGTTGGGGAAATCTGGAAGTG3',
product size 672/636 bp;

IGF-IR standard sense
                                    (SEQ ID NO. 3)
5'CCCTCACCATGGTGGAAAACGACCATATCCG3'
and antisense
                                    (SEQ ID NO. 4)
5'TGTGATATTGTAGGTGTCAGCTACCGTGGTGTTCC3',
product size 545.
```

One microgram of Calibrator cDNA (for definition of Calibrator cDNA, see "RNA Isolation Quantification and cDNA Synthesis" section of Materials and Methods), 45 µL of Platinum PCR SuperMix High Fidelity (Invitrogen, Carlsbad, Calif.), and 0.2 µM each of sense and antisense primers were used in the following PCR reaction: 94° C. for 2 minutes to denature cDNA followed by 35 cycles of 94° C. for 30 s, 55° C. for 30 s and 68° C. for 1 m. Products were analyzed on a 2% agarose gel run at 100V for 3.75 hours in order to separate products that represent IR-A and IR-B. Appropriate bands were subsequently gel purified using the MinElute Gel Extraction Kit, microcentrifuge protocol (Qiagen, Valencia, Calif.).

Two microliters of each purified product was cloned into the pCRII-TOPO vector (Invitrogen, Carlsbad, Calif.) using the protocol suggested for Chemical Transformation of *E. coli*. Two microliters of the ligated vector was used to chemically transform One Shot TOP10 competent cells (Invitrogen, Carlsbad, Calif.). Transformed cells were spread on 50 µg/ml ampicillin LB plates and incubated overnight at 37° C. Five positive colonies from each transformation were used to seed 3 ml LB+50 µg/ml ampicillin cultures. Cultures were grown overnight at 37° C. with shaking at 225 rpm. Plasmid DNA was isolated from three cultures per transformation using QIAprep Spin Miniprep Kit, microcentrifuge protocol (Qiagen, Valencia, Calif.). Plasmid DNA from insert-positive colonies was sequenced by the Molecular Resource Facility of UMDNJ using the SP6 primer. IR-A and IGF-1R plasmid sequences were compared for fidelity to NCBI sequences, gi:157057177 and gi:112983655, respectively. The previously unpublished mouse IR-B sequence was compared to the mouse IR-A sequence and the Rhesus monkey exon 11 sequence (accession number L42997) and submitted to NCBI under the accession number gi:170177902.

One microgram of plasmid DNA was linearized using the BglII restriction enzyme (Promega, Madison, Wis.) and analyzed on 1% agarose gel as above. Linear DNA was purified using the MinElute Reaction Cleanup Kit, microcentrifuge protocol (Qiagen, Valencia, Calif.) and quantified by spectrophotometry. Copy number was calculated using the following formula, [DNA concentration (g/µl)/(plasmid length (bp)*660)]*$6.022 \times 10^{23}$=molecules/µl. Linear plasmid DNA is referred to as standards for the purposes of this manuscript.

Q-PCR Primer Design and Optimization

IR-A, IR-B and IGF-1R Q-PCR primers were designed against the sequences listed above using Primer Premier v.5 Software (Premier Biosoft International, Palo Alto, Calif.) with attention to standard criteria for Q-PCR primer design (i.e.—all primers either span exon/exon junctions or anneal to two different exons to prevent interference from contaminating genomic DNA). Primer sequences and product sizes are as follows:

```
IR-A and IR-B sense
5'TCCTGAAGGAGCTGGAGGAGT3';      (SEQ ID NO. 5)

IR-A antisense
5'CTTTCGGGATGGCCTGG3',          (SEQ ID NO. 6)
product size 89;

IR-B antisense
5'TTCGGGATGGCCTACTGTC3',        (SEQ ID NO. 7)
product size 123;

IGF-1R sense
5'GGCACAACTACTGCTCCAAAGAC3'     (SEQ ID NO. 8)
and antisense
5'CTTTATCACCACCACACACTTCTG3',   (SEQ ID NO. 9)
product size 114.
```

β-actin primers were published previously (10). All primers listed above, were purchased from Integrated DNA Technologies, Inc. (Coralville, Iowa). Cytokeratin-18 (CK18), E-cadherin (E-cad), N-cadherin (N-cad) and βcasein pre-optimized QuantiTect Primer Assays were purchased from Qiagen (Valencia, Calif.).

To test the detection limit and efficiency of each primer pair, $10^7$ molecules/µl of each plasmid standard was serially diluted and used as template in Q-PCR assays with a dissociation stage and reaction conditions as described below to generate a standard curve of threshold cycle (Ct) value versus Log copy number. Efficiency was also evaluated from five independent reaction plates using two-fold dilutions of 200 ng Calibrator cDNA (see RNA isolation, quantification and cDNA synthesis section for description) as template.

For competition assays, $10^7$ copies of a non-specific plasmid DNA target was mixed with each standard and used as template in Q-PCR assays (e.g. to test IR-A primer specificity, $10^7$ copies of IR-B standard, or IGF-1R standard was mixed with each of the IR-A standard) and standard curves were generated as described above.

Further tests of assay specificity were performed on post-amplification Q-PCR products. Q-PCR products were taken directly from a post-amplification assay plate and analyzed by gel electrophoresis, a single band of size consistent with dissociation curve analysis was present for each assay (data not shown). Post-amplification products were also cloned, and sequences were confirmed against NCBI published sequences.

Q-PCR

The ΔΔCt method of relative quantification and SYBR green chemistry were used to measure expression of genes reported herein. β-actin was used previously as an endogenous control for analysis of kinase gene expression in mammary gland mRNA (11) and was used here because it displayed minimal variability between primary MEC samples.

All reactions were performed on the Applied Biosystems (ABI) 7900HT Fast Real-time PCR system using associated Sequence Detection Systems Software, Version 2.2.2 (ABI, Foster City, Calif.) or on the Applied Biosystems 7300 Real-time PCR system using SDS Software version 1.2.3. The thermal profile for all reactions was as follows: 50° C. for 2 minutes, 95° C. for 10 minutes, 40 cycles of 95° C. for 15 seconds and 58° C. (annealing temperature) for 1 minute. Unless otherwise indicated, IR-A, IR-B, IGF-1R, and β-actin reactions contained final concentrations of the following: 1× QuantiTect SYBR Green PCR Master Mix (Qiagen, Valencia, Calif.), 0.25 µM both sense and antisense primers and 50 ng cDNA. β-casein, CK18, E-cad and N-cad reactions contained 1×SYBR Green master mix, 1× QuantiTect primer assay mix and 50 ng cDNA. Q-PCR reactions performed to generate standard curves (i.e. for primer sensitivity tests and competition assays which used plasmid standards as template) were run using the absolute quantification assay and included a dissociation stage. Q-PCR reactions performed to quantify target gene expression were analyzed using the SDS relative quantification (ΔΔCt) assay and were combined into an SDS relative quantification (ΔΔCt) study to determine the expression of each target mRNA in primary MEC samples. All absolute quantification and ΔΔCt assays (except β-casein) were carried out at least twice and each sample was run in quadruplicate. Universal Mouse Reference RNA (Stratagene, La Jolla, Calif.) was the calibrator sample for all Q-PCR relative quantification studies except β-casein.

Human Insulin Receptor Isoform and IGF-1R Q-PCR Assay Development and Optimization Due to the small sequence difference between IR-A and IR-B and the high degree of sequence homology between the IGF-1R and IR mRNAs, primer design was critical to developing a Q-PCR assay to accurately detect all three receptors in human tissues. The validated mouse primers were not valid for detection of human receptors due to sequence differences between species. Moreover, distinct primers in different regions of the receptors were necessary for obtaining high sensitivity and specificity for the human receptor sequences. As for the mouse assay, we utilized an isoform-specific strategy identified by Vandenbroucke and colleagues [6] utilizing a primer that spans the exon junction specific to each isoform. For the human primers, we designed a common antisense primer that anneals within exon 12 to reduce inter-assay variability and obtain similar PCR kinetics. Specific sense primers were designed against exon/exon junctions unique to each isoform (FIG. 4A). IGF-1R primers were targeted to a region of low IR homology.

For primer sensitivity tests, 10-fold serial dilutions of plasmid standards were used as templates with each Q-PCR primer pair. A sample amplification plot of IR-A standards demonstrates these primers are accurate over six orders of magnitude from $10^7$ to 10 copies (FIG. 4B). IRB and IGF-1R assays were also accurate over seven orders of magnitude from $10^7$ to 10 copies (graphs not shown).

Competition assays were used to test the capability of the primers to specifically amplify their target in the presence of excess non-specific, homologous target, as may be the case when analyzing total RNA from a biological sample. Serial dilution of standards was repeated in a fixed excess of $10^7$ copies of competitor plasmid and standard curves were generated. FIG. 4C shows the standard curve from the IR-A amplification plot shown in FIG. 4B. Amplification plots were generated from serial dilution of IR-A standards in a fixed concentration of IR-B plasmid competitor or IGF-1R plasmid competitor (FIG. 4D). There was no significant change in IR-A amplification curves with addition of either competitor (slope=−3.32). Thus, there was no change in the IR-A standard curve resulting from this data indicating specific amplification of IR-A product. Similarly, the efficiency of IR-B and IGF-1R assays was not significantly changed in the presence of competition. These data demonstrate that the primers designed here are sensitive and precise to detect at least 100 copies of their target in the presence or absence of $10^7$ excess copies of highly homologous targets.

It is critical that efficiency of all primer pairs be approximately equivalent to allow accurate comparison of gene expression using the $\Delta\Delta C_t$ method of relative quantification (Applied Biosystems User Bulletin 2 P/N 4303859), therefore each primer pair designed for these studies was validated based on efficiency as well as sensitivity, and specificity. Primer efficiency is determined by the following equation: $E=[10^{-(1/slope)}]-1$; where slope is the slope of the standard curve when Ct value is plotted versus known amount of template, and $E=1.0$ when slope is approximately $-3.33$ (i.e. 100% reaction efficiency). The efficiencies of human IR-A, IR-B and IGF-1R primers are all approximately 100%. An additional test to determine if the efficiencies of the endogenous control primers and IR isoform and IGF-1R primers are suitably equivalent for the $\Delta\Delta C_t$ method of relative quantification is to plot the log cDNA dilution versus the $\Delta C_t$ value ($C_t$ of target–$C_t$ of endogenous control) and fit the data with a linear regression curve. According to Livak and Schmittgen [7], if the absolute value of the slope of the linear regression is close to zero, then the reaction efficiencies of the target and endogenous control genes are similar and the $\Delta\Delta C_t$ method of calculation can be applied. Primers for IR-A, IR-B, IGF1R and β-Actin were tested using 2-fold serial dilutions ranging from 200 ng to 12.5 ng of MDA-MB231 cDNA. The primer pairs of IR-A, IR-B and IGF1R were each tested for efficiency in relation to the endogenous control, β-Actin. IGF1R, with a sense primer concentration reduced to 0.05 μM, and β-Actin have approximately equivalent efficiencies, as the slope of the linear regression curve is $-0.0808$, meeting the criterion that the absolute value be less than 0.1 (FIG. 5). The slope of the linear regression curve for IR-B and β-Actin is approximately $-0.1$, the threshold for validation. The slope of the linear regression curve for IR-A and β-Actin is also at or below the threshold for validation. These values are below the value of 0.1 recommended in Applied Biosystems User Bulletin 2, indicating that the primers designed here for quantification of IR isoform and IGF-1R mRNA are suitable for use in the $\Delta\Delta C_t$ method of R.Q.

Specific Methods for Assay Development

Q-PCR plasmid standards for IR and IGF-1R were synthesized as described for the rodent assay but with the use of human-specific primers. Plasmid DNAs were cloned and sequenced to verify sequence for each standard. One microgram of plasmid DNA was linearized using the HindIII restriction enzyme (Invitrogen) and analyzed on 1% agarose gel. Linear DNA was purified using the MinElute Reaction Cleanup Kit, microcentrifuge protocol (Qiagen, Valencia, Calif.) and quantified by spectrophotometry. Copy number was calculated using the following formula, [DNA concentration (g/μl)/(plasmid length (bp)*660)]*$6.022 \times 10^{23}$=molecules/μl. Linear plasmid DNA is referred to as standards for the purposes of this manuscript.

Q-PCR Primer Design and Optimization

IR-A, IR-B and IGF-1R Q-PCR primers were designed against the human IR and IGF-1R sequences using Primer Premier v.5 Software (Premier Biosoft International, Palo Alto, Calif.) with attention to standard criteria for Q-PCR primer design. Primer sequences and product sizes are as follows:

```
IR-A and IR-B antisense
                                    (SEQ ID NO. 10)
  5'- GTC ACA TTC CCA ACA TCG CC -3';

IR-A sense
                                    (SEQ ID NO. 11)
  5'- TTT TCG TCC CCA GGC CAT C -3',
  product size 58 bp;

IR-B sense
                                    (SEQ ID NO. 12)
  5'- CCC CAG AAA AAC CTC TTC AGG -3',
  product size 87 bp;

IGF-1R sense
                                    (SEQ ID NO. 13)
  5'- GGC ACA ATT ACT GCT CCA AAG AC -3'

IGF-1R antisense
                                    (SEQ ID NO. 14)
  5'- CAA GGC CCT TTC TCC CAA C -3',
  product size 121 bp.
```

To test the detection limit and efficiency of each primer pair, $10^7$ molecules/μl of each plasmid standard was serially diluted and used as template in Q-PCR assays with a dissociation stage and reaction conditions as described below to generate a standard curve of threshold cycle (Ct) value versus Log copy number.

For competition assays, $10^7$ copies of a non-specific plasmid DNA target was mixed with each standard and used as template in Q-PCR assays (e.g. to test IR-A primer specificity, $10^7$ copies of IR-B standard, or IGF-1R standard was mixed with each of the IR-A standard) and standard curves were generated as described for the rodent assay.

Further tests of assay specificity were performed on post-amplification Q-PCR products. Q-PCR products were taken directly from a post-amplification assay plate and analyzed by gel electrophoresis, a single band of size consistent with dissociation curve analysis was present for each assay (data not shown). Post-amplification products were also cloned, and sequences were confirmed against NCBI published sequences.

Q-PCR

All reactions were performed on the Applied Biosystems (ABI) 7900HT Fast Real-time PCR system using associated Sequence Detection Systems Software, Version 2.2.2 (ABI, Foster City, Calif.) or on the Applied Biosystems 7300 Real-time PCR system using SDS Software version 1.2.3. The thermal profile for all reactions was as follows: 50° C. for 2 minutes, 95° C. for 10 minutes, 40 cycles of 95° C. for 15 seconds and 60° C. (annealing temperature) for 1 minute. IR-A, IR-B, IGF-1R, and β-actin reactions contained final concentrations of the following: 1× QuantiTect SYBR Green PCR Master Mix (Qiagen, Valencia, Calif.), 0.25 μM antisense and either 0.25 μM, 0.05 or 0.03 μM sense primers. Q-PCR reactions performed to generate standard curves (i.e. for primer sensitivity tests and competition assays which used plasmid standards as template) were run using the absolute quantification assay and included a dissociation stage.

REFERENCES CITED

1. Soos, M. A., Field, C. E., and Siddle, K. 1993 Purified hybrid insulin/insulin-like growth factor-I receptors bind insulin-like growth factor-I, but not insulin, with high affinity. Biochem J 290 (Pt 2):419-26.
2. Bailyes, E. M., Nave, B. T., Soos, M A., Orr, S. R., Hayward, A. C., and Siddle, K. 1997 Insulin receptor/IGF-I receptor hybrids are widely distributed in mammalian tissues: quantification of individual receptor species by selective immunoprecipitation and immunoblotting. Biochem J 327 (Pt 1):209-15.
3. Pandini, G., Frasca, F., Mineo, R., Sciacca, L., Vigneri, R., and Belfiore, A. 2002 Insulin/insulin-like growth factor I hybrid receptors have different biological characteristics depending on the insulin receptor isoform involved. J Biol Chem 277:39684-95.
4. Frasca, F., Pandini, G., Scalia, P., Sciacca, L., Mineo, R., Costantino, A., Goldline, I., Belfiore, A., and Vigneri, R. 1999 Insulin receptor isoform A, a newly recognized high-affinity insulin-like growth factor II receptor in fetal and cancer cells. Molecular and Cellular Biology 19:3278-3288.
5. Benyoucef, S., Surinya, K. H., Hadaschik, D., and Siddle, K. 2007 Characterization of insulin/IGF hybrid receptors: contributions of the insulin receptor L2 and Fn1 domains and the alternatively spliced exon 11 sequence to ligand binding and receptor activation. Biochem J 403:603-13.
6. Vandenbroucke, II, Vandesompele J, Paepe A D, Messiaen L 2001 Quantification of splice variants using real-time PCR. Nucleic Acids Res 29:E68-68
7. Livak K J, Schmittgen T D 2001 Analysis of relative gene expression data using real-time quantitative PCR and the 2(−Delta Delta C(T)) Method. Methods 25:402-408

---

The invention claimed is:

1. A quantitative PCR assay which differentiates between expression level of type 1 insulin-like growth factor receptor (IGF-IR), insulin receptor isoform A (IR-A), or insulin receptor isoform B (IR-B) within rodent tissues or cells comprising
   (a) providing sense and antisense primer pairs specific to IGF-IR, wherein said primer pairs are set forth in SEQ ID NO:8 and SEQ ID NO:9;
   (b) providing sense and antisense primer pairs specific to IR-A, wherein said primer pairs are set forth in SEQ ID NO:5 and SEQ ID NO:6;
   (c) providing sense and antisense primer pairs specific to IR-B, wherein said primer pairs are set forth in SEQ ID NO:5 and SEQ ID NO:7;
   (d) performing amplification of IGF-IR, IR-A, and IR-B; and
   (e) measuring the amount of IGF-IR, IR-A, and IR-B obtained relative to each other.

2. A kit for differentiating between expression level of rodent type 1 insulin-like growth factor receptor (IGF-IR), rodent insulin receptor isoform A (IR-A), or rodent insulin receptor isoform B (IR-B) comprising
   (a) sense and antisense primer pairs specific to IGF-IR, wherein said primer pairs are set forth in SEQ ID NO:8 and SEQ ID NO:9;
   (b) sense and antisense primer pairs specific to IR-A, wherein said primer pairs are set forth in SEQ ID NO:5 and SEQ ID NO:6; and
   (c) sense and antisense primer pairs specific to IR-B, wherein said primer pairs are set forth in SEQ ID NO:5 and SEQ ID NO:7.

* * * * *